United States Patent
Nutting et al.

(12) 
(10) Patent No.: US 6,733,489 B2
(45) Date of Patent: May 11, 2004

(54) VASCULAR ORIENTATION MARKER FOR DETERMINING THE ORIENTATION OF A BLOOD VESSEL

(75) Inventors: Charles Nutting, Phoenix, AZ (US); William M. Appling, Granville, NY (US); Arthur L. Zimmet, Centerport, NY (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 10/255,902

(22) Filed: Sep. 26, 2002

(65) Prior Publication Data

US 2004/0064042 A1 Apr. 1, 2004

(51) Int. Cl.$^7$ ............................................. A61M 25/098
(52) U.S. Cl. ....................................................... 604/529
(58) Field of Search ................................. 604/117, 529, 604/523, 524

(56) References Cited

U.S. PATENT DOCUMENTS

| | | | |
|---|---|---|---|
| 3,605,751 A | * | 9/1971 | Sheridan et al. ............ 604/529 |
| 4,279,252 A | * | 7/1981 | Martin ........................ 604/529 |
| 4,282,876 A | * | 8/1981 | Flynn ..................... 128/349 R |
| 4,577,637 A | * | 3/1986 | Mueller, Jr. ................. 128/658 |
| 4,588,399 A | * | 5/1986 | Nebergall et al. ............. 604/96 |
| 4,671,291 A | * | 6/1987 | Wilson ........................ 128/658 |
| 4,838,879 A | * | 6/1989 | Tanabe et al. .............. 604/280 |
| 5,045,071 A | * | 9/1991 | McCormick et al. ........ 604/280 |
| 5,045,072 A | * | 9/1991 | Castillo et al. ............. 604/280 |
| 5,203,777 A | * | 4/1993 | Lee ............................. 604/280 |
| 5,584,821 A | | 12/1996 | Hobbs et al. |
| 5,820,585 A | | 10/1998 | Mobin-Uddin et al. |
| 5,970,119 A | | 10/1999 | Hofmann |
| 6,086,548 A | | 7/2000 | Chaisson et al. |
| 6,224,609 B1 | | 5/2001 | Ressemann et al. |
| 6,283,950 B1 | | 9/2001 | Appling |

* cited by examiner

*Primary Examiner*—Sharon Kennedy
(74) *Attorney, Agent, or Firm*—Reed Smith LLP

(57) ABSTRACT

A catheter having one or more radio-opaque bands near the distal end is designed to be inserted into the renal artery so that the distal end of the catheter is adjacent to the origin of the renal artery. An X-ray image of the bands is used to position the X-ray head relative to the aorta and renal artery so that a useful, unobstructed radiological image perpendicular to the axis of the renal artery at its origin is obtained. This facilitates the positioning of a stent in the renal artery so that the stent encompasses the origin and extends no more than about three millimeters into the aorta. Two radio-opaque bands placed close to one another define a narrow radio-translucent band such that when the X-ray head is rotated to a position where parallax is reduced and the radio-translucent band can be imaged, the renal artery can be appropriately imaged without being obscured by the aorta.

13 Claims, 3 Drawing Sheets

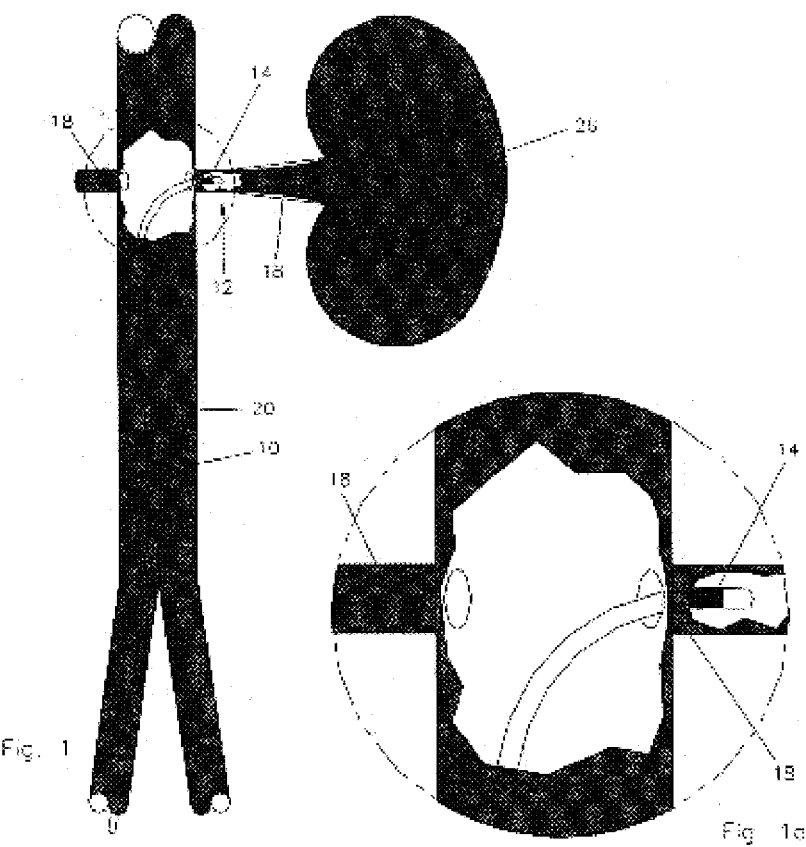
Fig. 1
Fig. 1a
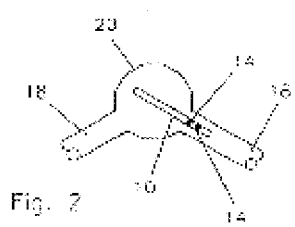
Fig. 2
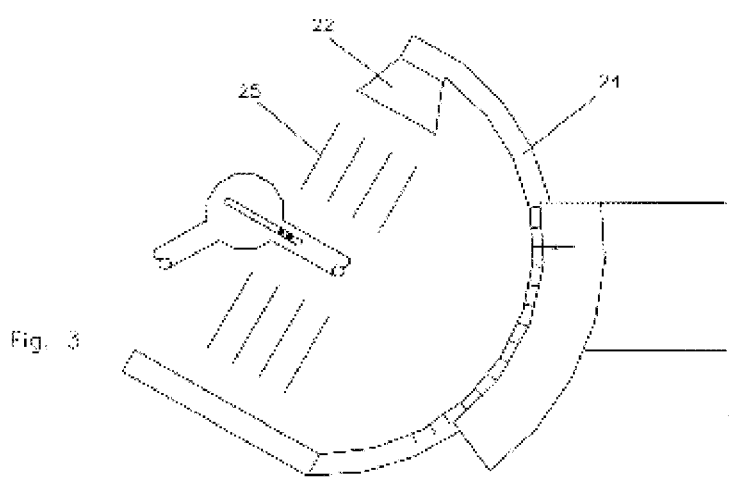
Fig. 3

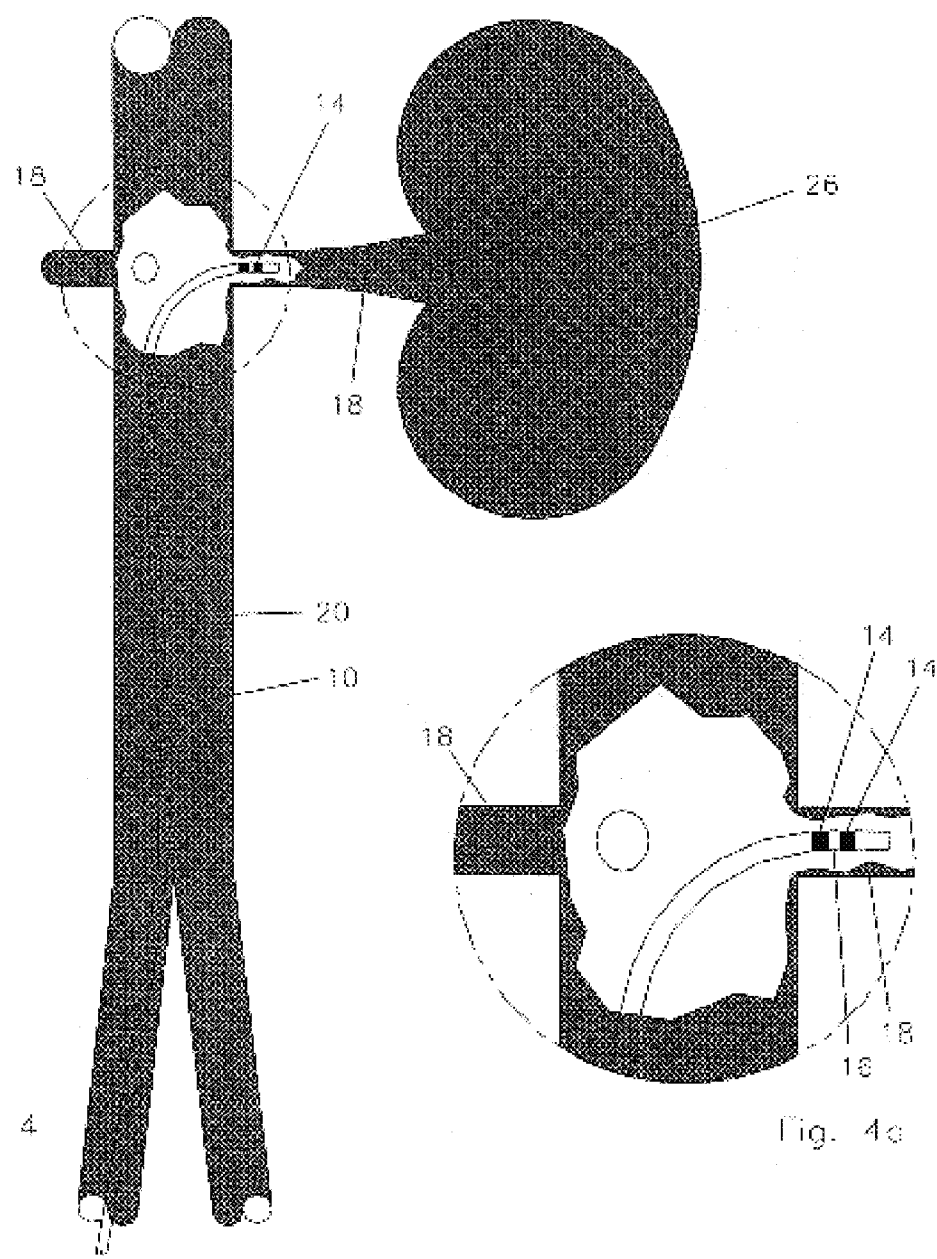
Fig. 4
Fig. 4a
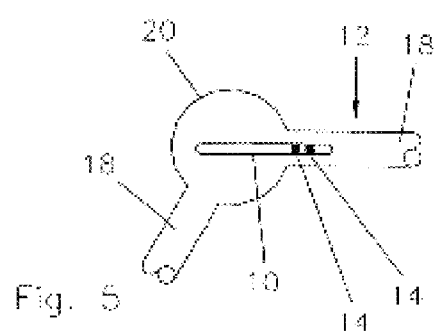
Fig. 5

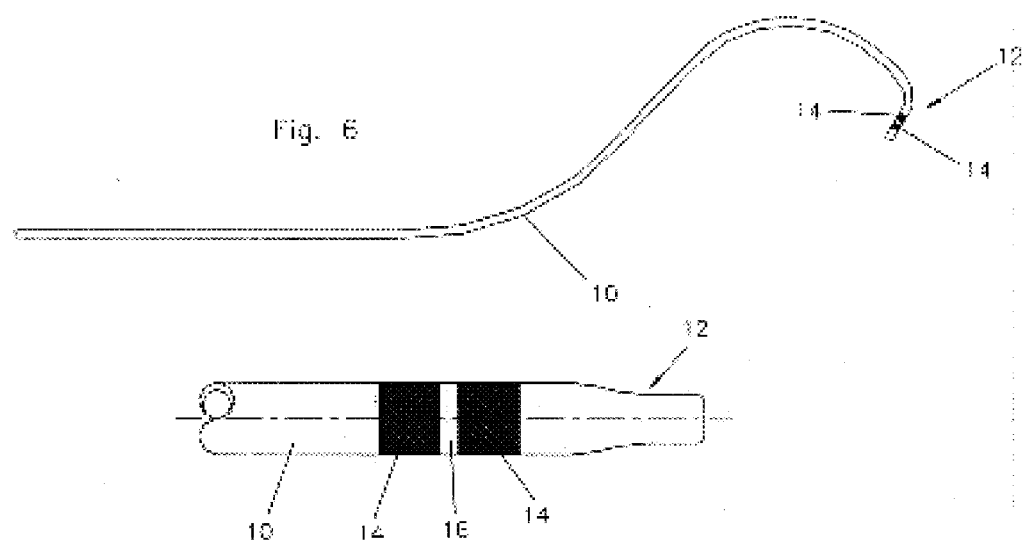
Fig. 6
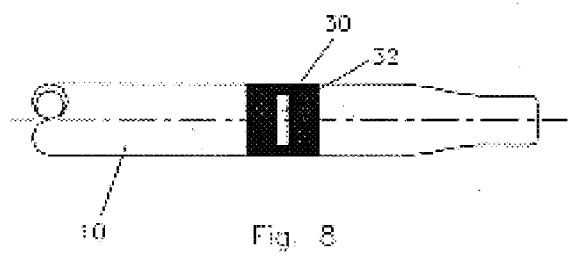
Fig. 7
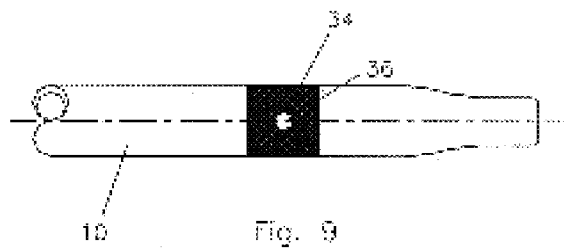
Fig. 8
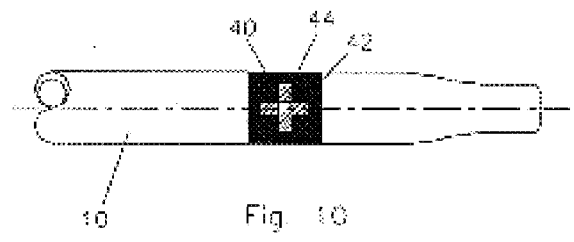
Fig. 9
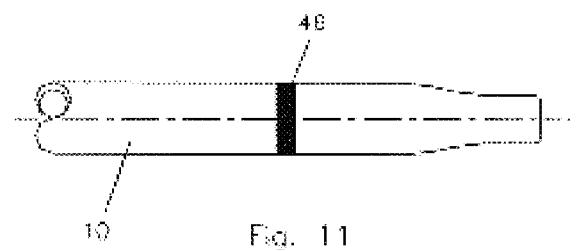
Fig. 10
Fig. 11

VASCULAR ORIENTATION MARKER FOR DETERMINING THE ORIENTATION OF A BLOOD VESSEL

BACKGROUND OF THE INVENTION

The present invention relates in general to therapies such as stenting. Specifically, the present invention relates to a vascular orientation marker which reduces parallax (radiological foreshortening) and enables the orientation of a blood vessel in a patient to be accurately visualized so that a stent can be accurately placed at the origin of the blood vessel.

Renal artery stenosis most commonly occurs at the junction of the aorta and the renal artery ostium. Lesions located at this junction are called renal ostial lesions. Unlike renal lesions located away from the aortic junction, ostial lesions do not respond well to transluminal renal angioplasty. Renal ostial lesions are technically difficult to dilate and have a high restenosis rate. Angioplasty with stent placement has been shown to have a higher clinical success rate in achieving and maintaining renal artery patency in ostial renal artery lesions.

Presently, when performing a stenting therapy, it is often difficult to determine the actual origin of a blood vessel. For example, the orientation of the renal artery is difficult to accurately determine during ostial renal stenting; which is when a stent is placed at the origin of a renal artery. The renal artery originates at the aorta and comes off the aorta at an angle towards the patient's back. The location at the aorta and the angle varies depending on the anatomy of each patient.

When a patient is radiographically imaged with the axis of the X-ray at a 90 degree angle to the flat surface on which the patient is lying, the image will not generally indicate the origin of the renal artery.

In particular, FIGS. 1 and 2 illustrate the origin of each of the renal arteries 18 at the aorta 20. If this arrangement is visualized fluoroscopically, the origin of each renal artery is obscured by the aorta.

It is extremely important during renal stenting that a stent be placed so that it covers the zone at the origin of the renal artery. This must be done without extending the stent out into the aorta by more than three millimeters. If the stent is placed extending further out in the aorta, the stent can disrupt aortic blood flow possibly leading to thrombosis. Devices being manipulated in the aorta secondary to stent placement can also disrupt the stent if the stent extends substantially into the aorta.

If the stent is placed too far into a renal artery, the stent will not adequately support the diseased area at the origin of that renal artery. To accurately place a stent at the origin of a blood vessel, and positions along the blood vessel must be visualized and to do so, the orientation of the blood vessel within the patient's body must be accurately determined.

Accordingly, it is an object of the present invention to provide a device which enables determining the position of the origin of a subsidiary blood vessel, such as the renal artery, relative to the surface of the more primary blood vessel, such as the aorta, off of which the subsidiary blood vessel extends.

It is a further related object of this invention to provide a method to accurately visualize the origin or orientation of a blood vessel within a patient's body. More specifically, by identifying the origin of the subsidiary blood vessel, enabling the position of an X-ray beam so that its direction of propagation will be perpendicular to the axis of the origin and thus provide a clear radiographic image showing the origin of the blood vessel; thereby permitting procedures, such as the positioning of a stent at the origin, to be accurately undertaken.

The use of radiopaque identifiers during fluoroscopic procedures are well known in the art. These identifiers can be in the form of markers, tape and other scaling devices. Radiopaque markers, spaced at pre-determined distances along the shaft of a catheter, are commonly used to determine the length of diseased segments of vascular structures. These catheters, also known as sizing devices, have no mechanism for ensuring perpendicular alignment between the markers and the X-ray beam. As a result, apparent length measurements may not equal the true length measurements.

U.S. Pat. No. 5,970,119 to Hofmann discloses a radiological scaling device which provides for calculation of sizes and lengths of anatomical structures. The device includes a mechanism for ensuring perpendicular alignment between the scale and the X-ray beam through the use of radio-lucent visualization gaps. The scaling device may be in the form of an externally placed strips, a catheter or adhesive tape. To determine the length or size of an anatomical structure, the apparent length/size of the radiopaque zone is first measured using fluoroscopy. Calculations of the difference between the apparent measured length and the true length of the radiopaque zone are then used to determine the actual length or size of the structure.

The '119 patent does not address a technique for determining the position of the origin of a subsidiary blood vessel relative to the source of the primary blood vessel off of which it extends. Nor, does the '119 patent teach or suggest a method for clearly visualizing the origin of a blood vessel so that procedures, such as the positioning of a stent, can be accurately undertaken.

BRIEF DESCRIPTION

Disclosed is a catheter having one or more radio-opaque bands near its distal end. The catheter is inserted in the renal artery. An X-ray image of the bands is used to determine the position of the renal artery relative to the aorta. This determination facilitates proper insertion of a stent at the origin of the renal artery.

In one presently preferred embodiment, two annular radio-opaque bands are placed at the distal end of the catheter body. On a 0.067 inches (1.70 mm) diameter catheter, the bands are each 0.040 inches (1.02 mm) wide and are spaced from one another by 0.006 inches (0.15 mm). This provides a 0.006 inches (0.15 mm) radio-translucent band bounded by first and second radio-opaque bands.

When the distal end of the catheter is inserted into a renal artery, the radiologist can orient an X-ray machine until the two radio-opaque bands are clearly imaged and differentiated from one another. This means that the X-ray machine is properly aligned relative to the axis of the bands on the catheter and thus the direction of X-ray propagation is perpendicular to the axis of the renal artery. Such alignment provides an image that appropriately identifies the origin of the renal artery. For accurate stent placement at the origin of the renal artery, the physician must be able to determine the renal artery's take off angle from the aorta within plus or minus five degrees.

A stent may then be placed accurately at that origin because the image provided by the X-ray machine is so oriented that it will show the proximal end of the stent aligned with the origin of the renal artery.

Also disclosed are alternate embodiments of the vascular orientation marker of this invention. These alternate embodiments have various radio-opaque features at the distal end of the catheter employed.

One such example is a single radio-opaque band, which therefore is surrounded by radio-translucent zones. The radiologist can determine appropriate orientation when the single band is imaged as having a uniform minimum image width.

Other embodiments employ a radio-opaque band having radio-translucent portions 180° displaced from one another. The X-ray machine is positioned so that these portions are aligned with the axis of projection to provide an image of the radio-translucent portion. This provides an indication of a proper alignment between the X-ray machine and the renal artery.

BRIEF DESCRIPTION OF THE FIGURES

FIG. 1 is a schematic illustration of the aorta and two renal arteries. FIG. 1a is a larger scale view of the area where the marker catheter of this invention is in place in one of the renal arteries. FIGS. 1 and 1A represent fluoroscopic images in which the zones of the marker are not in image registry.

FIG. 2 is a cross-sectional schematic of FIG. 1 through the two renal arteries.

FIG. 3 is a schematic illustration showing the position of the X-ray machine relative to the FIG. 2 illustration of aorta, renal artery and marker catheter.

FIG. 4 is a schematic illustration, similar to that of FIG. 1, along a plane perpendicular to the main axis of the X-rays, in which the X-ray head has been rotated so that the plane of the opening into one of the renal arteries is parallel to the main axis of the X-ray beam.

FIG. 4a is a larger scale view of the area where the marker catheter of this invention is in place showing the marker adjacent the origin of a renal artery.

FIG. 5 is a schematic cross-section of FIG. 4 through the two renal arteries.

FIG. 6 is a longitudinal view of a first, and presently preferred, embodiment of this invention. This embodiment is illustrated in FIGS. 1–5.

FIG. 7 is an enlarged view of the distal portion of the FIG. 6 marker catheter.

FIG. 8 is a view, like that of FIG. 7, of the distal portion of a second embodiment of the marker catheter of this invention.

FIG. 9 is a view, like that of FIG. 7, of the distal portion of a third embodiment of the marker catheter of this invention.

FIG. 10 is a view, like that of FIG. 7, of the distal portion of a fourth embodiment of the marker catheter of this invention.

FIG. 11 is a view, like that of FIG. 7, of the distal portion of a fifth embodiment of the marker catheter of this invention.

DESCRIPTION OF THE PREFERRED EMBODIMENTS

A preferred embodiment of this invention is disclosed in FIGS. 1 through 7. As best seen in FIGS. 6 and 7, a catheter 10 has a distal portion 12 having first and second radio-opaque bands 14 separated by a radio-translucent band 16. The bands 14 are preferably 360° circumferential bands which are made out of known radio-opaque material and are bonded by known techniques to the catheter 10 substrate. In one embodiment having a catheter 10 diameter of 0.067 inches (1.70 mm), the radio-opaque bands 14 have a width of about 0.040 inches (1.02 mm) and are separated from one another so as to provide a radio-translucent band 16 of 0.006 inches (0.15 mm).

This provides the ability to orient the perpendicularity of the axis X—X of the bands to the direction of the axis of X-ray transmission so that these two axes are in orthogonal directions within plus or minus five degrees.

In another embodiment, having a diameter in which the catheter 10 has a diameter of 0.105 inches (2.67 mm), two 0.040 inches (1.02 mm) radio-opaque bands 14 are spaced apart to provide a radio-translucent band 16 of 0.009 inches (0.23 mm). This also provides the desired orthogonal orientation within plus or minus five degrees.

The maximum radio-translucent gap dimension for a specific catheter diameter can be determined using the following calculation:

Tangent $A = W/D$ where $A$ = desired angle of accuracy, $W$ = width of the radio-translucent gap and $D$ = diameter of the catheter.

FIGS. 1–5 schematically show two renal arteries 18 branching off of the aorta 20. In one of these renal arteries 18, the catheter 10 of this invention is shown in which the distal portion 12 is close to the origin of the renal artery 18.

As shown in FIG. 2, the two renal arteries 18 that are directed to the two kidneys are not diametrically opposed to one another. It should be noted that they are not in a predetermined angular relationship to the circumference of the aorta 20.

When a stent (not shown) is to be placed in a renal artery 18, it is often important that the stent extend to the origin of the renal artery 18 but not extend more than three millimeters into the aorta 20. In order to assure that the stent is properly positioned, the surgeon requires the kind of image illustrated schematically in FIGS. 4 and 4a. As shown in FIG. 4, the renal artery 18 in which the stent to be placed is imaged so that the origin of the renal artery can be readily viewed. To achieve this imaging, the X-ray head 22 (see FIG. 3) is rotated on the C-arm 24 to a position where the translucent band 16, defined by the two radio-opaque bands 14 (see FIG. 7), is oriented relative to the X-rays 25 so that the translucent band 16 is visible in the radiologic image. This visibility occurs when circumferentially opposed portions B of the band 16 are in image registry. When the X-ray head 22 is in that position, then the renal artery 18, in which the catheter 10 is positioned, will be imaged, as shown in FIG. 4, so that its origin is not obscured by the aorta 20.

As a consequence, the image of the ends of the stent can be more clearly distinguished in terms of their position within the renal artery 18. More specifically, the stent can be positioned so that it is within the renal artery 18 and so that the proximal end of the stent does not project more than one millimeter into the aorta 20.

The stent that is inserted is normally in the range of fifteen millimeters in length and should extend into the aorta 20 by about one millimeter (mm). This will assure that the origin of the rental artery 18 is held open while minimizing potential damage to the stent and minimizing disruption of blood flow in the aorta. It is known to be undesirable to have the stent extend much more than three millimeters into the aorta. Extension of the stent into the aorta may make it difficult to remove the placement balloon without distorting the stent. Also, patients often require other activity which requires placement of catheters through the aorta. If a stent is in the way, the stent might be damaged and/or the catheter blocked.

The radio-opaque bands 14 should be located within the zone where the stent is to be located. This will normally provide a radiological image of the renal artery and aorta which facilitates appropriate placement of the stent.

The Geometric Context of the Invention.

The device of this invention operates because there is a predetermined geometric relationship between (a) the plane of the table on which the patient lies, (b) the axis of the X-ray machine's C-arm 24 around which axis the X-ray head 22 revolves and (c) the axes of the patient's spine and aorta. These geometric relations are approximate, but close enough to permit effective use of this invention.

The aorta is parallel to the spine. When a patient is lying on an X-ray table, the patient is oriented so that the axis of the spine and therefore the axis of the aorta are parallel to the axis of the C-arm 24. Thus the axis of the aorta is perpendicular to the direction in which the X-rays are projected. More specifically, the axis of the aorta is parallel to the plane of the image created by the X-ray projection.

Under those conditions, rotation of the X-ray head on the C-arm will at some point bring the direction of projection (i.e., central axis) of the X-rays parallel to the plane of the origin of the renal artery 18. This position will be indicated to the radiologist because on the X-ray image, the radio-translucent gap 16 between the two radio-opaque bands 14 will be visible.

Because the axis of the renal artery 18 may not be, and frequently is not, perpendicular to the opening into the aorta of the origin of the renal artery, it is important that the radio-opaque bands 14 be close to the origin of the renal artery so that the approximate geometric relationships referenced above will be maintained.

More explicitly, the following geometric relationships are obtained:

The axis for the C-arm rotation is parallel to the axis of the aorta.

The above is readily obtained because the axis of the aorta and the axis of the backbone are substantially parallel.

The central axis of the X-ray beams is in a direction that is perpendicular to the axis of the C-arm and thus of the aorta.

The plane of the origin of the renal artery is parallel to the central axis of the X-ray beam when the marker of this invention indicates appropriate alignment.

Thus a stent in the renal artery can be positioned so that it extends to the origin of the renal artery without extending into the aorta by more than a small predetermined amount such as one millimeter.

FIG. 8 shows a second embodiment of this invention in which a radio-opaque band 30 contains two circumferentially opposed radio-translucent slots 32. When the slots 32 are in radial alignment and also aligned with the direction of the X-ray projection, the slots 32 will appear on the radiologic image, one through the other. When in image registry; that is, when the slot 32 image appears, the orientation of the X-ray is such as to provide the image of the renal artery 18 as shown on in FIG. 4a.

One advantage of the FIG. 8 embodiment is that it permits providing a single band 30 with precut slots 32 to make the catheter assembly easier and repeatable.

FIG. 9 shows a third embodiment in which the catheter 10 has a single circumferential radio-opaque band 34 and two radio-translucent holes 36 which are circumferentially opposed to one another. In use, aligning the X-ray beam until the holes 36 are visible, one through the other, (i.e., in image registry) on the radiologic image indicates the correct X-ray head orientation to provide the FIG. 4a type imaging.

FIG. 10 shows a fourth embodiment in which a radio-opaque band 40 contains a first longitudinal radio-translucent slot 42 and a second circumferential radio-translucent slot 44. These two slots 42 and 44 are circumferentially positioned so that the center portion of the two slots are in radial alignment with one another. The center position will provide a radio-translucent image when the X-ray head 22 is positioned to provide the FIG. 4a type of imaging.

FIG. 11 shows a fifth embodiment in which a single radio-opaque band 46 is on the catheter 10. When the band 46 is imaged on the radiologic image with minimum width, there will be an indication of the appropriate alignment of the X-ray head 22 to the renal artery 18 axis and origin. To achieve minimum image width, the circumferentially opposed portions of the band 46 must be in full image registry. The FIG. 11 embodiment would require more in the way of careful adjustment of the X-ray head 22 on the C-arm 24 to obtain this minimum width image of the band 46. Thus it would be somewhat more difficult to apply and require greater care than the preferred embodiment illustrated in FIG. 7.

Radio-contrast Zone.

The term radio-contrast zone is used herein to refer to that area on the catheter body which contrasts with the surrounding area in terms of radio-opacity or radio-translucence. Thus in the FIG. 7 preferred embodiment, the radio-contrast zone is the annular radio-translucent band 16 between two radio-opaque bands 14.

In the FIG. 11 embodiment, the radio-contrast zone is a single annular radio-opaque band 46 on the radio-translucent catheter 10.

In the other embodiments disclosed, the radio-contrast zone is provided by a set of two radio-translucent zones within a radio-opaque band wherein the radio-contrast zones are in 180° circumferential registry with one another.

Band.

The band is a circumferential band of either radio-opaque material or radio-translucent material defined by radio-opaque bands. The bands are preferably annular. It should be understood that there are designs in which something less than a 360° annular band could be employed to provide the alignment which is the object of this invention; even though less than full annular bands are not preferred. Such embodiments would be more difficult to use and would not provide the easiest observable indications of alignment that the preferred embodiments of this invention provide.

While the foregoing description and drawings represent the presently preferred embodiments of the invention, it should be understood that those skilled in the art will be able to make changes and modifications to those embodiments without departing from the teachings of the invention and the scope of the claims.

For example, the marker catheter could have further features which would make it an interventional or diagnostic catheter. It could be configured as part of a guiding catheter, a stent delivery system or a balloon catheter. It could be configured as a sheath. It should be understood herein that the reference to a catheter in the claims encompasses all such configurations and any other such body that extends into the vascular system.

What is claimed is:

1. The artery orientation marker comprising:
    a catheter body,
    a substantially annular radio-opaque band on said body,
    a plurality of substantially radio-translucent zones deployed along a circumference within said radio-opaque band, two of said zones having diametrically opposed portions, said radio-translucent zones having a sufficiently narrow width so that when two of said radio-translucent zones are visualized in alignment in a fluoroscopic image, an indication of orientation of said catheter body at the location of said band to the axis of transmission of the fluoroscopic beam is provided within a predetermined angular limit, whereby, said indication of orientation is adequate to provide a visualization of the origin of the artery involved when said band is near the origin.

2. The marker of claim 1 wherein said two of said zones are displaced 180° from each other.

3. The marker of claim 2 wherein said two of said zones are geometrically congruent.

4. The marker of claim 1 wherein said narrow width is less than approximately 0.23 mm.

5. The marker of claim 1 wherein said narrow width is between approximately 0.15 mm and 0.23 mm.

6. The marker of claim 3 wherein said narrow width is between approximately 0.15 mm and 0.23 mm.

7. The marker of claim 3 wherein said narrow width is between approximately 0.15 mm and 0.23 mm.

8. The method of visualizing the origin of an artery comprising the steps of:

inserting the marker of claim 1 into an artery, and rotating an X-ray head encompassing the origin of the artery until said two of said radio-translucent zones of said marker are visualized in alignment in an X-ray image.

9. The method of claim 8 wherein said two of said radio-translucent zones are geometrically congruent.

10. The method of claim 8 wherein said narrow width is less than approximately 0.23 mm.

11. The method of claim 8 wherein narrow width is between approximately 0.15 mm and 0.23 mm.

12. The method of claim 9 wherein said narrow width is between approximately 0.15 mm and 0.23 mm.

13. The method of claim 9 wherein said narrow width is between approximately 0.15 mm and 0.23 mm.

\* \* \* \* \*

UNITED STATES PATENT AND TRADEMARK OFFICE
CERTIFICATE OF CORRECTION

PATENT NO.    : 6,733,489 B2  
DATED         : May 11, 2004  
INVENTOR(S)   : Charles Nutting and William M. Appling Page 1 of 1

It is certified that error appears in the above-identified patent and that said Letters Patent is hereby corrected as shown below:

<u>Title page,</u>
Item [75], Inventors, delete inventor "Arthur L. Zimmet" by replacing
-- Charles Nutting, Phoneix, AZ (US); William M. Appling, Granville, NY (US); Arthur L. Zimmet, Centerport, NY (US)" with -- Charles Nutting, Phoneix, AZ (US); William M. Appling, Granville, NY (US) --.

Signed and Sealed this

Nineteenth Day of October, 2004

JON W. DUDAS
*Director of the United States Patent and Trademark Office*